(12) United States Patent
Akashe et al.

(10) Patent No.: US 6,479,684 B1
(45) Date of Patent: Nov. 12, 2002

(54) PROCESS FOR STRUCTURING LIPIDS AND THE STRUCTURED PRODUCTS THEREOF

(75) Inventors: Ahmad Akashe, Mundelein, IL (US); Manuel Marquez, Prospect Heights, IL (US)

(73) Assignee: Kraft Foods Holdings, Inc., Northfield, IL (US)

(*) Notice: Subject to any disclaimer, the term of this patent is extended or adjusted under 35 U.S.C. 154(b) by 57 days.

(21) Appl. No.: 09/799,996

(22) Filed: Mar. 6, 2001

(51) Int. Cl.[7] .............................................. C07C 51/00
(52) U.S. Cl. ...................................... 554/154; 504/124
(58) Field of Search ................................. 554/124, 154

(56) References Cited

U.S. PATENT DOCUMENTS 4,957,757 A    9/1990 Law et al. ................... 426/281
6,011,131 A    1/2000 Sato et al. ................... 528/170

FOREIGN PATENT DOCUMENTS

EP    0 209 509    2/1987
JP    6-305956    11/1994

*Primary Examiner*—Deborah Carr
(74) *Attorney, Agent, or Firm*—Fitch, Even, Tabin & Flannery

(57) ABSTRACT

The present invention generally relates to a process for hardening lipids, especially unsaturated lipids such as unsaturated fatty oils, by mixing and interacting lipids with polyamines such that the peak melting point of the resulting combination is higher than that of the lipid alone. In this way, the polyamine-treated unsaturated lipid can be converted into a solid or semi-solid state at a relatively lower temperature than the unsaturated lipid alone. The lipid and polyamine combination displays physical attributes that mimic the crystalline structures of saturated lipids and fats without the incurring the associated negative health implications of such saturated lipids and fats.

27 Claims, 4 Drawing Sheets

PROCESS FOR STRUCTURING LIPIDS AND THE STRUCTURED PRODUCTS THEREOF

FIELD OF THE INVENTION

The present invention generally relates to processes for structuring lipids, especially unsaturated lipids, using polyamines and the composite structured products obtained thereby.

BACKGROUND OF THE INVENTION

Fats are esters of glycerol with fatty acids which can be isolated from a number of plant, animal, and marine life sources. Processes for chemically synthesizing fats also are known. Triglycerides are the predominant fat constituent of most naturally-occurring fats and oils. The terms "oils" or "fatty oils," as used herein, mean liquid fats, unless indicated otherwise.

Fats, such as triglycerides, have physical characteristics which depend upon a number of different factors, such as the types, lengths, isomeric configuration, and degree of unsaturation of the various fatty acid chain groups present, and the type and conditions of processing to which the fat is subjected. As a general rule of thumb, for a given type of fat, a saturated version thereof typically has a higher melting point than its unsaturated analogs. Generally such saturated fat molecules can fit together more closely and can form intermolecular bonds. Consequently, more energy will be required to break and melt such saturated fats. By comparison, unsaturated fats generally can not structurally fit together as well, at least partially due to the 30° bend or "kink" present at cis configuration carbon-carbon double bonds in the fatty acid chains of an unsaturated fat. This typically results in reduced intermolecular forces, and a concomitant lower melting temperature for the unsaturated fat.

Among other things, solid and semi-solid forms of fats have been used extensively in the food processing and food service industries. For example, solid and partially solid forms of fat have been used to improve the stabilities of various food products and deep frying fats. They also have been used to improve the texture and consistency of spreads, margarines, and the like. However, many forms of useful fats are obtained in oil form. These oils include, for example, many naturally occurring vegetable, animal, and fish oils. Consequently, interest has long existed in finding and developing processes for converting such fatty oils into solid or semi-solid forms. Such "hardening" processes decrease the proportion of liquid fat relative to solid fat in the processed fat, thereby reducing the melting point.

Hydrogenation is a known practical technique for hardening fatty oils, including unsaturated triglycerides. Hydrogenation is typically carried out catalytically under appropriate heat and pressure conditions to convert all, or at least some, of the carbon-carbon double bonds into carbon-carbon single bonds, thereby reducing the degree of unsaturation in the fat. As a result, once the hydrogenation reaction progresses sufficiently, the partially or fully hydrogenated oil is converted into a solid or semi-solid form with a higher melting temperature than the untreated precursor. Hydrogenation also renders the fat less susceptible to oxidative rancidity and increases the thermal stability of the fat.

Hydrogenation not only reduces the degree of unsaturation in the fat, but it also can result in other significant alterations in the molecular structure of the processed oil. For instance, the cis configuration of the carbon-carbon double bonds is more prevalently found in naturally-occurring fats rather than the trans configuration. However, and depending on processing conditions, hydrogenation often can result in the conversion of such cis carbon-carbon double bonds present in the fatty acid chain groups into the trans configuration. Cis or trans positional isomers, wherein one or more of the double bonds relocates to a new position along the fatty acid chain group, can also occur. Unfortunately, such structural changes resulting from hydrogenation are not necessarily benign, especially where the processed oil is destined for edible product uses.

As widely known and reported in recent years, a number of clinical and epidemiological studies have linked increased consumption of saturated fats with possible adverse health implications, especially in terms of increasing the risk of cardiovascular heart disease and/or aggravating such conditions. Replacement of saturated fats in a diet with polyunsaturated fats has been suggested to result in lower cholesterol levels, and in reducing low-density lipoprotein (LDL) levels in particular. Elevated levels of LDL cholesterol in the bloodstream are generally associated with increased risk of coronary heart disease. Additionally, high levels of trans fatty acids in a diet, whether from saturated or unsaturated fats, also have been associated with increases in blood levels of LDL cholesterol. Therefore, hardening of oils by reducing their degree of unsaturation, such as by hydrogenation, has drawbacks from at least dietary and health standpoints, not to mention the processing costs involved.

Triglycerides can also be prepared by esterification of glycerol using fatty acids. Such synthetic methods can also lead to products having some of the same problems as natural triglycerides discussed above.

As can be appreciated, their remains a need for techniques of hardening unsaturated fatty oils that avoid or significantly reduce the problems typically associated with hydrogenation. The present invention fulfills this need, as well as other objectives, by a unique process for structuring unsaturated lipids using polyamines without hydrogenation.

SUMMARY OF THE INVENTION

The present invention provides a process for treating unsaturated lipids by mixing them with an effective amount of a polyamine. An effective amount is an amount sufficient to increase the melting point of the resulting treated lipid composition to a temperature higher than that of the original untreated lipid. Generally, the practice of this invention allows a melting point of at least about 1° C. higher than the melting point of the original lipid, preferably about 1 to about 70° C. higher than the melting point of the original lipid, and more preferably about 5 to about 25° C. higher than the melting point of the original lipid. As a consequence, this invention makes it possible to harden unsaturated lipids and convert them into solid or semi-solid forms having lower melting points than the untreated lipids. Moreover, this result is achieved without hydrogenation and without the dietary and health defects often associated with hydrogenation of unsaturated lipids.

The present invention also provides a composition having a new composite molecular structure composed of the unsaturated lipid and polyamine constituents of the mixture. The resulting lipid and polyamine composite molecular structure is thermally reversible and, thus, can be controlled and/or modified by the temperature (thermal energy) applied to the mixture. As an added advantage, polyamine constituents of the composite molecular structure can also provide other desirable properties to the compositions of the present invention. For instance, the polyamine can provide antimicrobial activity, preservative activity, thermal stability, and/or photo stability. In this way, the treated lipid is better protected against degradation.

The unsaturated lipids that can be treated with polyamine according to the present invention include, for example, unsaturated monoglycerides, unsaturated diglycerides, unsaturated triglycerides, fatty acids, fatty alcohols, phosphatides, sterols, fat-soluble vitamins, terpenes, and mixtures thereof. Although the present invention can be used with saturated lipids, it is generally preferred that it is used with unsaturated lipids, and even more preferably with unsaturated triglycerides, to obtain the most benefit. Preferred fatty oils used in the present invention are lipids having at least some unsaturation in at least one hydrocarbon chain. Suitable unsaturated lipids include, for example, readily available vegetable, animal, and marine oils containing long chain fatty acids. The invention is especially useful in the treatment of unsaturated triglyceride oils, polyunsaturated fatty acid oils, and other fatty acid oils.

The polyamines suitable for treating lipids, especially unsaturated lipids, according to the present invention generally include aliphatic polyamines. Especially preferred are aliphatic, linear polyamines of the general formula:

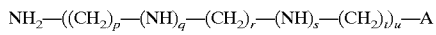

$$NH_2-((CH_2)_p-(NH)_q-(CH_2)_r-(NH)_s-(CH_2)_t)_u-A$$

wherein u is an integer of 1 to 5; p, r and t independently are integers of 0 to 8, with the proviso that at least one of p, r, and t is greater than or equal to 2; wherein q and s independently are 0 or 1; and wherein A is an amino group, a hydroxyl group, or a fluoro group, with the proviso that, when A is hydroxyl or fluoro, at least one of q and s is 1. In a preferred embodiment, an aliphatic polyamine entity is used for processing the lipid according to the invention. The aliphatic amine preferably is nonsubstituted in order to minimize steric effects. Especially preferred aliphatic polyamines are biocompatible, naturally occurring polyamines such as spermine, spermidine, and putrescine.

The effective amount of polyamine combined with the unsaturated lipid can vary depending on the type of polyamine and lipid involved in the combination, as long as it is sufficient to increase the melting point of the mixture to a value above that of the untreated unsaturated lipid. If the polyamine addition amount is too low, the melting point of the mixture will be that of the lipid component (or perhaps even lower on account of free polyamine present). Generally, the addition of at least about 1 percent polyamine, based on the combined weight of the polyamine and lipid, will be sufficient to provide the desired intermolecular interactions and physical changes on the lipid. Preferably the amount of polyamine added is about 1 to about 30 percent, and more preferably about 3 to about 10 percent. Preferably, the polyamine and lipid are combined without using an solvent in order to enhance direct contact between the mixed polyamine and lipid. If desired, other components such as, for example, flavorants, spices, colorants, and the like can be incorporated.

The compositions of the present invention can be prepared by simply mixing the components without elaborate or expensive process arrangements or equipment. Generally, such mixing is carried out at about 0 to about 100° C., preferably at about 20 to about 50° C., using simple agitation. Agitation during the initial stages of mixing is especially helpful. When performed at room temperature, the desired interaction of the polyamine and lipid may require about ten hours or more achieve the desired composite molecular structure, and thereby induce a higher melting temperature via the resulting structured lipid product. Although the temperature of the mixture can be increased above room temperature to accelerate the process, it is generally preferred that the temperature be kept at about room temperature to minimize oxidation.

The present invention also is directed to the lipid-polyamine mixtures containing the unique structured lipid products obtained by the process described herein. Additionally, the solid and semi-solid forms of the polyamine-treated unsaturated lipids prepared according to this invention are suitable for many and varied applications including, for example, food processing, food products, cosmetics, medicinal or cosmetic topical ointments, medicinal or cosmetic topical lotions, medicinal or cosmetic topical creams, personal care products, and the like.

BRIEF DESCRIPTION OF THE DRAWINGS

Other features, and advantages of the present invention will become apparent from the following detail description of preferred embodiments of the invention with reference to the drawings, in which:

FIG. 1A is a low magnification image with large field of view; FIG. 1B is a medium magnification image; and FIGS. 1C and 1D are higher magnification images showing details of crystal aggregates.

FIG. 2A is a low magnification image with large field of view; FIG. 2B is a medium magnification image; and FIGS. 2C and 2D are higher magnification images showing details of crystal aggregates.

FIG. 3A is a low magnification image with large field of view; FIG. 3B is a medium magnification image; and FIGS. 3C and 3D are higher magnification images showing details of crystal aggregates.

FIG. 4A is a low magnification polarized image with large field of view; FIG. 4B is a medium magnification image using DIC optics showing non-crystalline material in relation to crystal aggregates; FIG. 4C is a medium magnification polarized image showing the crystal components of the aggregates; and FIGS. 4D and 4E are higher magnification images showing details of crystal aggregates using polarized and brightfield optics, respectively.

FIG. 5A is a low magnification polarized image with large field of view; FIG. 5B is a medium magnification image using DIC optics showing non-crystalline material in relation to crystal aggregates; FIG. 5C is a medium magnification polarized image showing the crystal components of the aggregates; and FIGS. 5D and 5E are higher magnification images showing details of crystal aggregates using polarized optics.

FIG. 6A is a low magnification polarized image with large field of view; FIG. 6B is a medium magnification image using DIC optics showing non-crystalline material in relation to crystal aggregates; FIG. 6C is a medium magnification polarized image showing the crystal components of the aggregates; and FIGS. 6D and 6E are higher magnification images showing details of crystal aggregates using polarized optics.

DETAILED DESCRIPTION OF THE INVENTION

Figure 1:
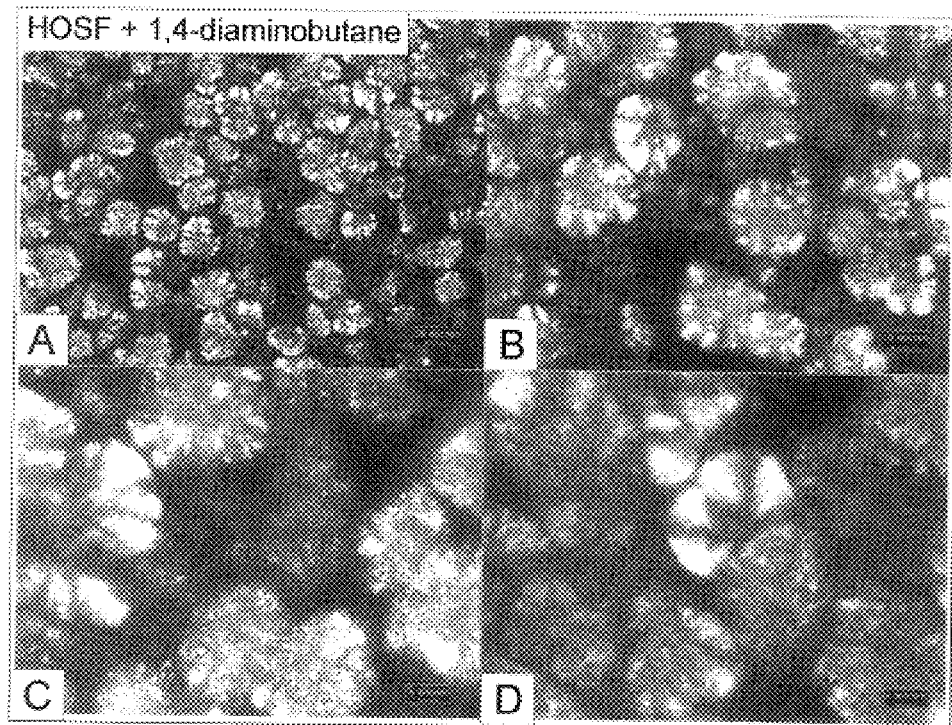
FIG. 1 is a set of microphotographs using polarized light of a composition containing high oleic sunflower oil (HOSF) and 1,4-diaminobutane at room temperature. The composition was prepared according to the method of Example 1.
Figure 2:
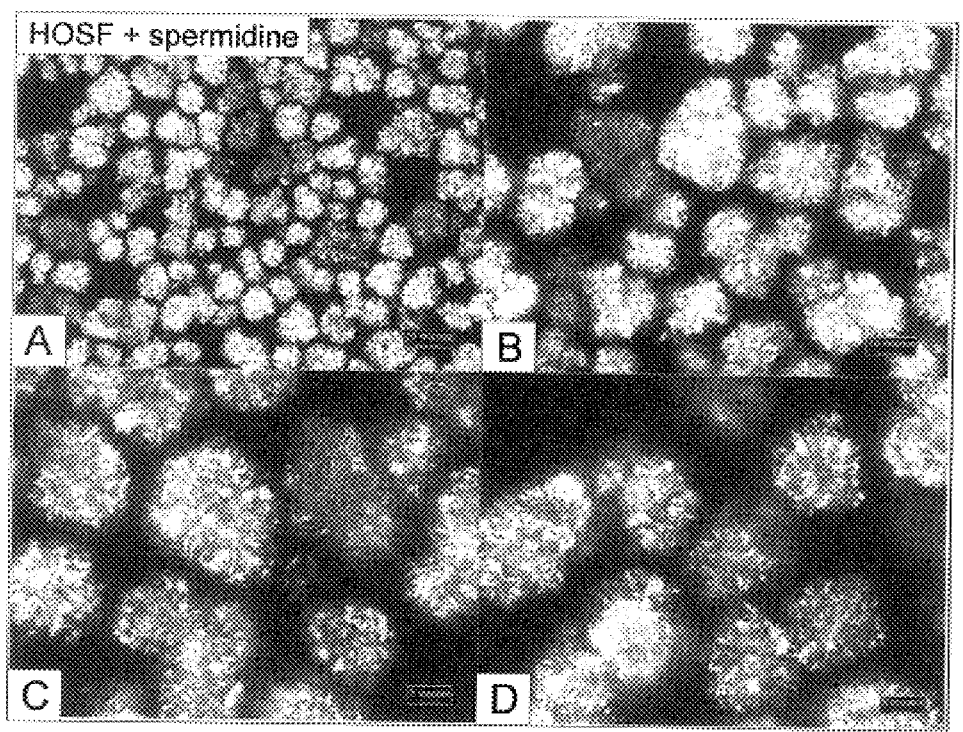
FIG. 2 is a set of microphotographs using polarized light of a composition containing high oleic sunflower oil (HOSF) and spermidine at room temperature. The composition was prepared according to the method of Example 1.
Figure 3:
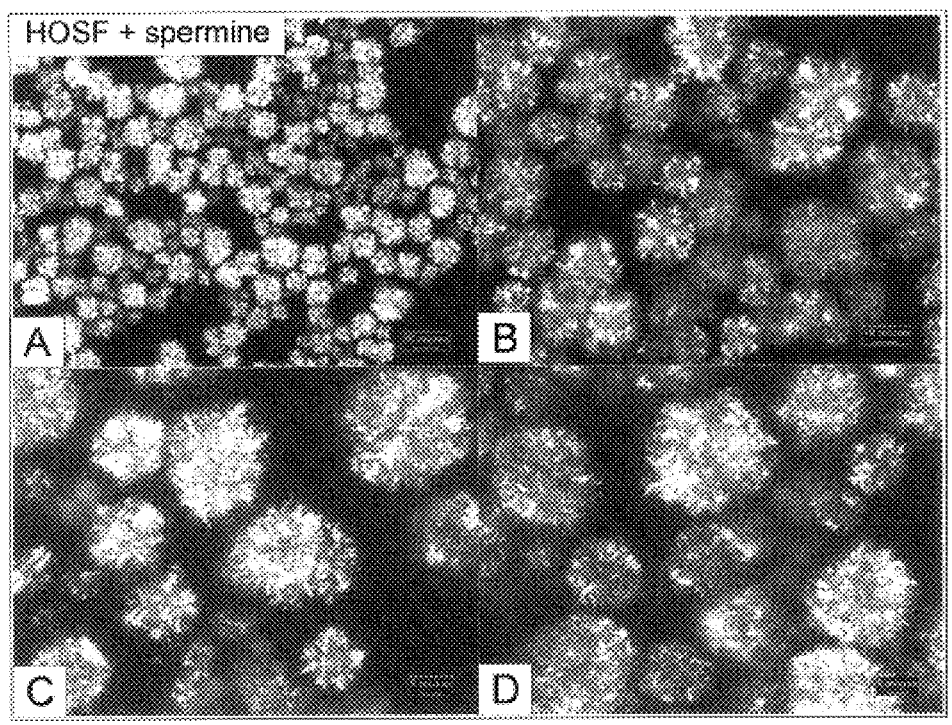
FIG. 3 is a set of microphotographs using polarized light of a composition containing high oleic sunflower oil (HOSF) and spermine at room temperature. The composition was prepared according to the method of Example 1.
Figure 4:
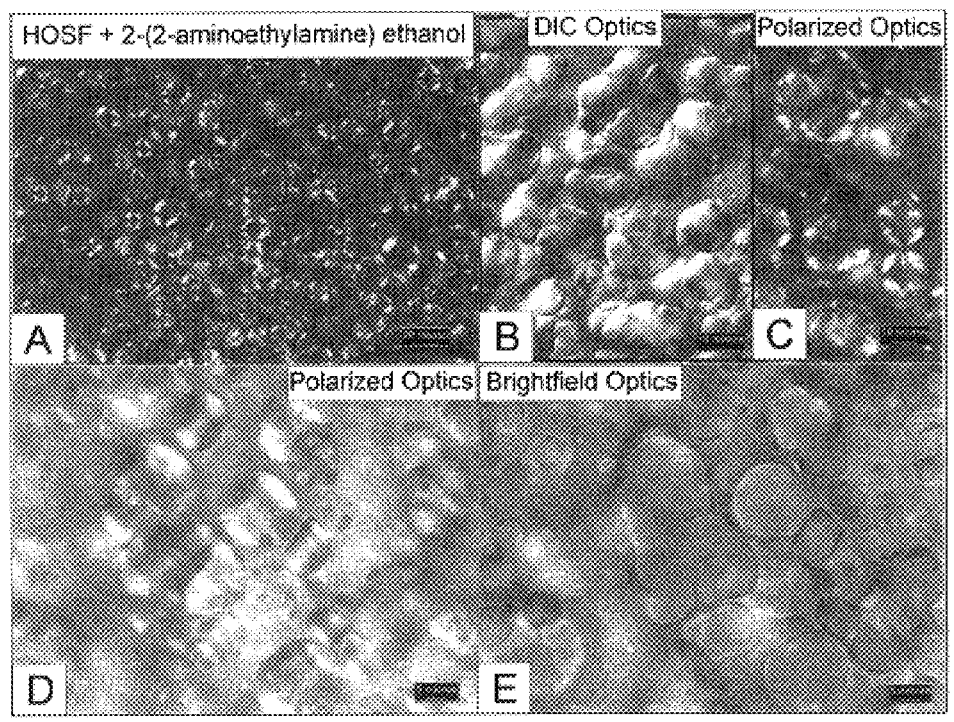
FIG. 4 is a set of microphotographs of a composition containing high oleic sunflower oil (HOSF) and 2-(2-amino ethylamine) ethanol at room temperature. The composition was prepared according to the method of Example 1.
Figure 5:
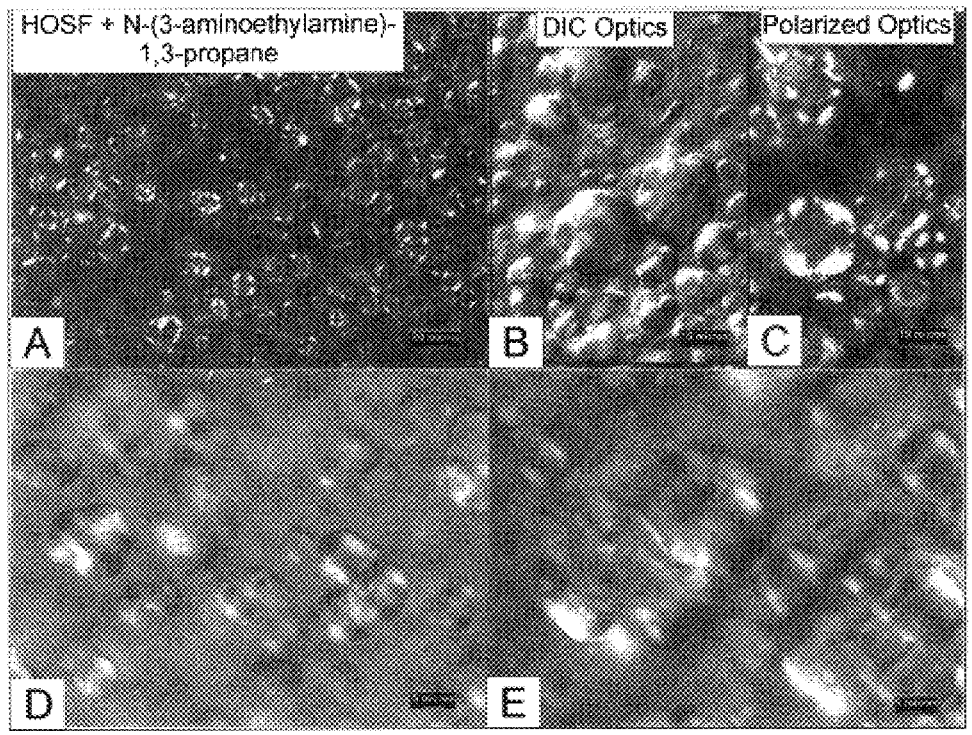
FIG. 5 is a microphotograph of a composition containing high oleic sunflower oil (HOSF) and N-(3-aminopropyl)-1,3-propane at room temperature. The composition was prepared according to the method of Example 1.
Figure 6:
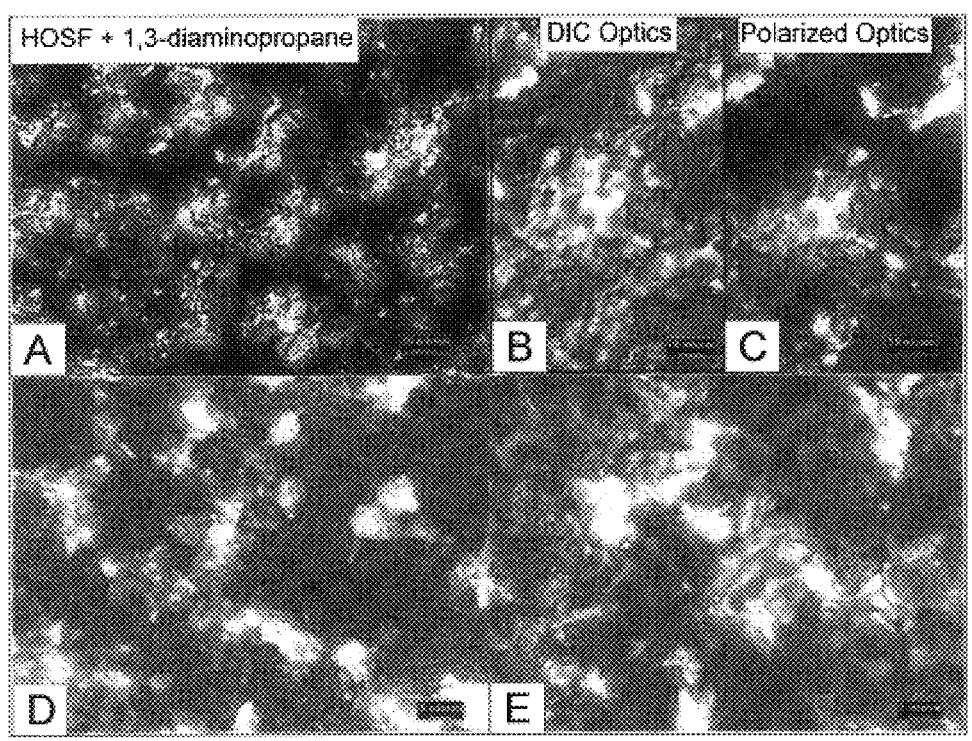
FIG. 6 is a microphotograph of a composition containing high oleic sunflower oil (HOSF) and 1,3-diaminopropane at room temperature. The composition was prepared according to the method of Example 1.

Generally, the present invention provides a process for treating lipids, especially unsaturated lipids, by their direct physical admixture with polyamines in an amount effective such that the resulting treated lipid hardens at a higher temperature than would otherwise be possible in the absence of the inventive treatment. The invention also is directed to the product of that process as a new material.

The present invention makes it possible to manipulate, modify, and tailor certain physical properties of lipid oils, such as percent solids and/or rheology, by inducing a change in melting point. This change is effected without changing the degree or nature of unsaturation in the lipid. This invention is particularly applicable to the conversion of liquid lipids, especially unsaturated liquid lipids, solid or semi-solid forms.

Unsaturated lipids that can be treated with a polyamine according to the present invention include, for example, unsaturated monoglycerides, unsaturated diglycerides, unsaturated triglycerides, fatty acids, fatty alcohols, phosphatides, sterols, fat-soluble vitamins, terpenes, and minutes thereof. Unsaturated lipid oils comprising fatty acids and lipids incorporating fatty acid moieties are of particular interest and suitability for use in the present invention. The fatty acid chains in these lipid oils can be straight, branched, or ring structures. Preferably, the fatty acid chains are straight hydrocarbon chains ("straight" embraces cis and/or trans main chain configurations). It is preferred that the fatty acids or lipids containing fatty acid moieties are amphipathic. Examples of suitable unsaturated lipids include many readily available vegetable, animal, and marine oils containing long chain fatty acids or moieties thereof. The invention is especially useful in the treatment of unsaturated triglyceride oils, polyunsaturated fatty acid oils, and other long chain unsaturated fatty acid oils. Again, lipid oils having straight alkyl chains in the fatty acid moieties are preferred.

Suitable unsaturated triglycerides can be represented by general formula I:

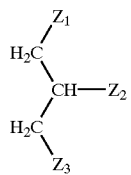

in which $Z_1$, $Z_2$, and $Z_3$ represent fatty acid moieties, which can be the same or different from one another, and with the proviso that at least one of $Z_1$, $Z_2$, and $Z_3$ contains at least one carbon-carbon double bond. The fatty acid moieties $Z_1$, $Z_2$, and $Z_3$ can be derived from fatty acids of the unsaturated and saturated types, although at least one must be derived from an unsaturated fatty acid. Examples of suitable unsaturated fatty acids include caroleic acid, lauroleic acid, myristoleic acid, palmitoleic acid, oleic, elaidic, vaccenic acid, linoleic, linolenic acid, gadoleic, arachidonic acid, and erucic acid. Examples of the saturated fatty acids include acetic acid, butyric acid, caproic acid, caprylic acid, capric acid, lauric acid, myristic acid, palmitic acid, stearic acid, arachidic acid, behenic acid, eicosapentaenoic acid, docosenoic, and docosahexaenoic acid. For diglycerides, one among $Z_1$, $Z_2$, and $Z_3$ represents a hydroxyl group instead of a fatty acid moiety; and for monoglyceride, two among $Z_1$, $Z_2$, and $Z_3$ represent a hydroxyl group in a suitable.

Suitable unsaturated triglycerides are more specifically shown in formula II below:

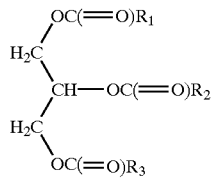

where $R_1$, $R_2$, and $R_3$ are hydrocarbon chains, where $R_1$, $R_2$, and $R_3$ can be the same or different from one another, and where at least one of $R_1$, $R_2$, and $R_3$ includes at least one carbon-to-carbon double bond. These chains $R_1$, $R_2$, and $R_3$ can be aliphatic hydrocarbon chains or alicyclic hydrocarbon groups. The aliphatic chains can be straight or branched chains, but preferably are straight. The acid chains $R_1$, $R_2$, and $R_3$ in formula II generally contain from about 2 to about 22 carbon atoms, preferably from about 8 to 18 carbon atoms.

Suitable fatty acids and esters of glycerides for use in this invention can be obtained from natural sources or can be prepared synthetically. Naturally occurring sources of unsaturated triglycerides, typically as mixtures thereof, include, for example, high oleic sunflower oil, sunflower oil, rapeseed oil, soybean oil, peanut oil, canola oil, cottonseed oil, coconut oil, palm oil, palm kernel oil, corn oil, flax seed oil, olive oil, safflower oil, lard oil, castor oil, fish oil, milk fat, beef tallow oil, and the like, as well as mixtures thereof. Especially preferred triglycerides for use in the present invention include high oleic sunflower oil, sunflower oil, soybean oil, canola oil, corn oil, flax seed oil, olive oil, and fish oil.

Free fatty acids, such as those identified above, also can be used as the lipid to be treated with polyamine according to the invention. Also, polyunsaturated fatty acids found in fish oils, such as cod liver oil and capelin oil, are suitable as the lipid to be treated.

For purposes of the descriptions herein, the degree of unsaturation of a lipid (e.g., fat) corresponds to the number of carbon-carbon double bonds present, and can be expressed in terms of the iodine value of the fat. The iodine value is calculated as the number of grams of iodine that will react with 100 grams of the fat and can be calculated from the resulting composition by gas chromatography. For purposes of this invention, the terminology "saturated," as used to characterize fats or free fatty acids, refers to the absence of carbon-carbon double bonds in fatty acid moieties.

In order to harden the unsaturated lipids without the need to modify (i.e., decrease) unsaturation in the fats, or increase the presence of trans fatty acid isomeric configurations in the fat, the lipids are mixed and interacted with polyamines according to this invention. The polyamines useful in this invention generally are aliphatic polyamines. Preferred aliphatic polyamines for this invention are represented by the following general formula III:

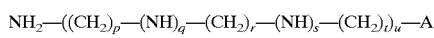

wherein u is an integer of 1 to 5; p, r and t independently are integers of 0 to 8, with the proviso that at least one of p, r, and t is greater than or equal to 2; wherein q and s independently are 0 or 1; and wherein A is an amino group, a hydroxyl group, or a fluoro group, with the proviso that, when A is hydroxyl or fluoro, at least one of q and s is 1.

Suitable aliphatic polyamines include alkylene diamines, alkylene triamines, alkylene tetraamines, alkylene pentamines, alkylene hexamines, iminobis alkylamines, and so forth. Illustrative, non-limiting examples of suitable aliphatic polyamines include ethylenediamine, diethylenetriamine, triethylenetetraamine, pentaethylenehexamine, putrescine ($H_2NCH_2CH_2CH_2CH_2NH_2$), cadaverine ($H_2NCH_2CH_2CH_2CH_2CH_2NH_2$), spermidine ($H_2NCH_2CH_2CH_2CH_2NHCH_2CH_2CH_2NH_2$), spermine ($H_2NCH_2CH_2CH_2NHCH_2CH_2CH_2CH_2NHCH_2CH_2CH_2NH_2$), iminobis ethylamine, iminobis propylamine, 2,(2-aminoethylamino)ethanol, N-(3-aminopropyl)-1,3-propanediamine, 1,3-diaminopropane, 1,4-diaminobutane, N,N'-bis(3-aminopropyl)-1,3-propanediamine, and the like. Preferred polyamines include putrescine, spermidine, spermine, and mixtures thereof.

The polyamines suitable for use in this invention generally are liquids at room temperature. Numerous commercial sources exist for polyamines identified herein as being suitable in the practice of the invention. Also, certain naturally-occurring linear aliphatic polyamines, such as spermine and others, can be extracted from whey protein concentrates obtained from the production of cheese from milk. Such polyamines in whey protein concentrate can be isolated by ultrafiltration using a cation-exchange resin that selectively adsorbs polyamines, which are then eluted with an acid or salt solution, followed by neutralization to obtain a polyamine solution. Polyamines can be characterized by gas chromatographic techniques, for example, known in the art.

The polyamine and lipid can be combined in any suitable vessel or container of sufficient holding volume space. Generally no special handling precautions or measures are needed. The effective amount of polyamine to be combined with the lipid, preferably the unsaturated lipid, can vary depending on the type of polyamine and lipid involved, as long as it is sufficient in amount to induce the outcome of raising the peak melting point of the treated lipid. The peak melting point of the treated lipid can be measured in the mixture with differential scanning calorimetry (DSC). By comparing the DSC thermogram of the untreated lipid of interest with that of the polyamine-treated version according to this invention, differences and changes in melting point can be easily assessed and confirmed. The thermograms of the polyamine-treated lipids of this invention tend to have more rounded peaks (as opposed to generally very sharp peaks for the thermograms of the individual components) in the melt endotherm regions. Nonetheless, a single peak melting point value is normally readily identifiable in the thermograms of the mixtures made according to the invention. The more rounded peaks observed in the melt endotherm peak regions of the thermograms generated for the polyamine-treated lipids of this invention are thought to be indicative of, and consistent with, the presence of a composite or semi-crystalline material.

If the polyamine addition level is too low, the melting point of the lipid in the mixture will remain unchanged, and the solid content of the mixture will be lower on account of the liquid polyamine present. On the other hand, if additional or excess amounts of polyamine are added to the unsaturated lipid after the melting point change already has been identified, the further additions of the polyamine have no further benefit, and can even become detrimental at a certain level as they will increase the fluidity of the mixture. Generally, the addition amount of polyamine necessary to impart the change in melting point of the lipid will represent at least about 1 percent, and more preferably between about 3 and 10 percent, of the combined weight of the polyamine and lipid in order to induce the desired intermolecular interactions and physical changes on the lipid.

Preferably, the combination of polyamine and lipid is performed without the use of any solvent or dispersing medium other than the lipid ingredient itself, so as to enhance the direct contact between the mixed materials. A further advantage of the present invention is that the processing can be performed over a rather broad and flexible range of temperatures, including room temperature, without the need for elaborate or expensive process arrangements. The suitable mixing temperatures generally range from about 0 to about 100° C., preferably from about 10 to about 40° C., and more preferably from about 20 and about 30° C.

Care should be taken to ensure complete mixing of the lipid and polyamine ingredients after they are initially combined in a vessel using any convenient mechanical or manual means or method. When the mixing is performed at approximately room temperature (i.e., about 20 to about 30° C.), the desired interaction of the polyamine and lipid may require up to approximately ten hours or more following initial mixing until sufficient standing time is afforded to permit the lipid and polyamines to assemble and organize together in manners described herein, and thereby provide structured lipid product having a higher melting temperature than the untreated lipid. Alternatively, the temperature of the mixture can be increased above room temperature to accelerate the process. It is not necessary to continue agitation or stirring of the mixture while it stands. Preferably, the mixture is left to stand without being agitated.

After the lipid and polyamine are mixed and permitted to stand, the presence of the desired result can confirmed by DSC analysis (as detailed above) and/or polarized light microscopy. When examined using light microscopy, the lipid-polyamine mixtures prepared according to the invention generally contain a plurality of discrete, light-reflecting inclusions or particles, while the untreated lipid appears transparent, under polarized light. Also, the respective solid and liquid fractions of the mixture can be measured and compared to those of the untreated lipid at the same temperature to check for differences in solid content.

While not desiring to be bound to any particular theory, it nonetheless is believed that the unsaturated lipid molecules interact reversibly with the polyamine molecules via intermolecular, noncovalent forces or bonds to form a composite structural matrix on a molecular level. Aliphatic, linear polyamines are thought to have a two-fold effect in bringing about the unique intermolecular interaction with unsaturated lipids. First, the aliphatic, linear polyamines are thought to align with respect to each other in the mixture containing the lipid. More particularly, the polyamines are thought to align via noncovalent bonding, and in particular, via dipole-dipole interactions, such as hydrogen bonding, between terminal or end groups of separate polyamine molecules. These end groups will be selected from amine, hydroxyl, and/or fluoro groups, which are amenable to dipole-dipole interactions. Second, this end-to-end association is propagated through a number of separate polyamine molecules, ultimately leading to the formation of large linear assemblies of polyamines, which are noncovalently and reversibly linked together at their ends. A sufficient concentration of polyamines are present in the lipid medium such that this end-to-end arrangement of a series of polyamine molecules can form linear template-like structures including numerous alkylene chain segments available for close approach and mutual interaction with corresponding hydrocarbon chain segments presented on the lipids. In this way, a large number of these polyamine templates will form in the predominant lipid medium.

These polyamine templates are thought to increase the opportunity for an orderly occurrence of mutual chain-to-chain interactions between the linear hydrocarbon chain or fatty acid chain segments on the unsaturated lipid molecules and the many linear hydrocarbon (i.e., alkylene) chain segments offered along the polyamine templates. In free, unsaturated lipid molecules, such as triglycerides, free rotation is possible about most if not all the bonds of the fatty acid chains. However, in the mixture prepared according to this invention, it is thought that the linear hydrocarbon chain or fatty acid chain segments in the unsaturated lipid molecules are able to closely approach, assemble and bind together non-covalently with the hydrocarbon chain segments presented by the polyamine templates. Non-covalent bonding there between is thought to be achieved by van der Waals forces or similar intermolecular forces.

The result is a composite molecular structure of polyamine and lipid molecules assembled into a highly organized, matrix-like structure. As a consequence, the lipid molecules are effectively made stiffer by such interactions and assemblage between the hydrocarbon chain segments thereof with the chain segments in the polyamine templates, as they will have restricted freedom of movement and mobility. The result is something analogous to a conformal assembly of monolayers.

It also appears preferable to select polyamines having substantially regular and consistent spacing of the amine groups along the polyamines. That is to say, the polyamines are preferably selected to provide intervening hydrocarbon chain segments located between the primary amino, hydroxyl, or fluoro end groups which are substantially the equal in length, when the polyamines used have an uninterrupted hydrocarbon chain segments between such end groups. For polyamines having one or more secondary amino groups (imino positions) interposed between such end groups and along the alkylene main chain, it is preferred that each alkylene chain segment is substantially the same in the total number of carbon positions (e.g., ≦two carbon difference for a given polyamine). In this way, variability is reduced in the polyamine sites and lengths thereof made available to the lipids to approach and associate with.

An important advance embodied by the present invention is that a pseudo-crystalline character is induced in unsaturated lipids. This pseudo-crystallinity manifests itself in increased melting properties and rheologies (e.g., viscosities, consistencies, textures), which are suitable for uses in many industrial and consumer products, including food products, that rely upon and incorporate solid and semi-solid fats as ingredients. These applications include edible products, medicinal or cosmetic topical ointments, medicinal or cosmetic lotions, medicinal or cosmetic creams, hair products, lubricants, soaps, lubricated papers, and the like. The fatty oils or lipids treated with polyamine according to the invention generally can be used in any of those applications as a partial or complete substitute for saturated solid or semi-solid fat content otherwise needed or useful.

The inventive lipid-polyamine composite matrix product also avoids the dietary and health concerns raised by hardened fats obtained by reducing the degree of unsaturation in the oils and/or increasing the presence of trans isomeric configurations in the lipid. Moreover, the polyamines used in the invention can be "multi-functional." For example, in addition to serving as templates with which the lipids can form a reversibly "hardenable" composite matrix, the polyamines also can impart anti-microbial, anti-oxidative, anti-allergy, immune related, preservative effects (e.g., photo-stability, thermal stability, and microbial stability), and/or other desirable effects to the composite structural matrix. Examples of such "multi-functional" polyamines include spermine and spermidine.

As discussed above, the composite structural matrix formation phenomenon of the lipid and polyamine mixture components often necessitates affording standing time spanning several or more hours, especially if carried out at room temperature or below, to provide sufficient time for the lipid and polyamine molecules to organize and assemble into the desired composite matrix structure. Thus, it is preferable to first form the lipid-polyamine matrix structure according to the present invention and then add the resulting composition to the final product in which it is to be used. In this way, the risk is diminished of introducing the polyamines or lipids in such a free, highly dispersed form that they cannot organize according to the mechanisms described herein.

The Examples that follow are intended to illustrate, and not to limit, the invention. All percentages used herein are by weight, unless otherwise indicated.

EXAMPLE 1

This example illustrates the effect on the liquid-solid physical state of the fatty oil high oleic sunflower oil (HOSF) by treatment with various types of polyamine compounds according to the invention. Samples 1–7 were prepared by mixing the desired polyamine with the high oleic sunflower oil in an appropriately sized glass vial. The high oleic sunflower oil had a melting point of less than about 25° C. The following polyamines were used:

| | | Melting Point (° C.) |
|---|---|---|
| AEAE | 2,(2-aminoethylamino)ethanol | <25 |
| APPD | N-(3-aminopropyl)-1,3 propanediamine | <25 |
| DAP | 1,3-diaminopropane | <25 |

-continued

| | | Melting Point (° C.) |
|---|---|---|
| DAB | 1,4-diaminobutane | ~29 |
| SMD | Spermidine | ~28 |
| SM | Spermine | ~28–30 |
| BAPPDA | N,N'-bis(3-aminopropyl)-1,3-propane-diamine | <25 |

Most of these polyamines are liquids at room temperature and all have a melting point temperature higher than the high oleic sunflower oil. Each sample was formulated with about 6 percent polyamine and 94 percent high oleic sunflower oil. Mixing of the polyamine and high oleic sunflower oil was conducted at room temperature (approximately 25° C.) for each sample. No solvent or dispersion medium were used. Each polyamine-sunflower oil mixture was initially shaken by hand for about 60 seconds in the capped vial. The temperature of the resulting mixture after shaking was not noticeably different from that of the individual ingredients immediately before their combination. The mixture was then allowed to stand for about 12 hours at about 25° C. No observable changes were visible to the naked eye in the physical appearance of the mixture immediately upon admixture of the lipid and polyamine. After standing overnight, the samples appeared slightly opalescent to varying degrees.

Figure 7A:
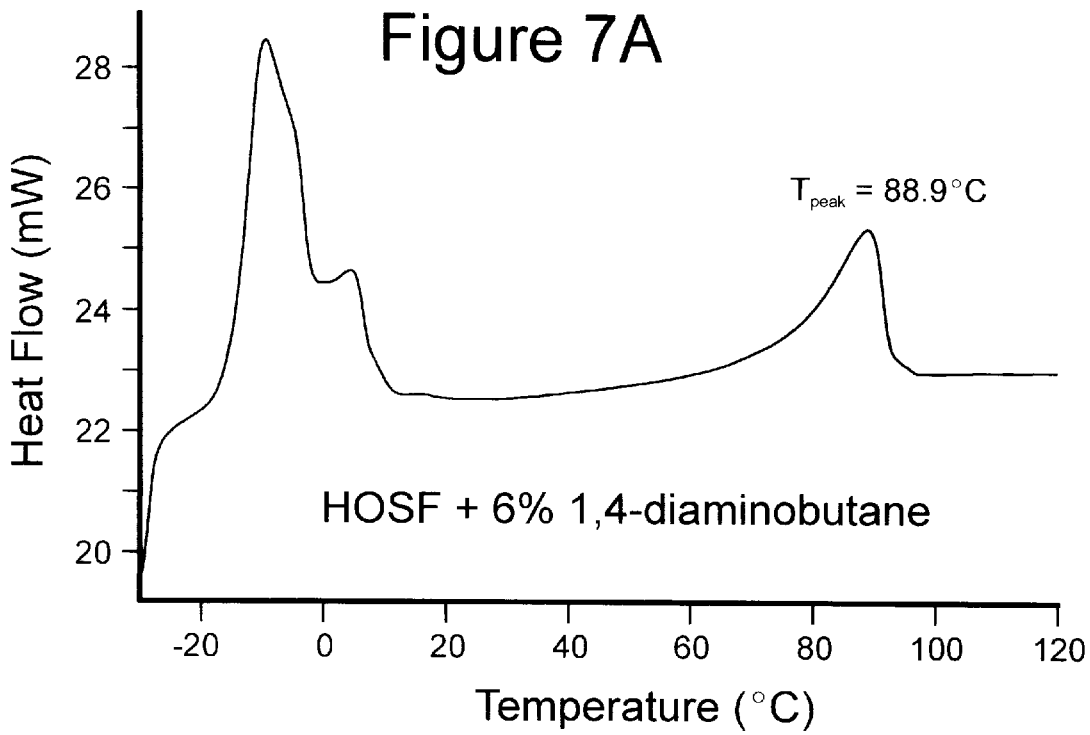
FIG. 7 provides DSC thermograms for (A) a composition containing high oleic sunflower oil (HOSF) and 1,3-diaminobutane prepared according to the method of Example 1 and (B) a composition containing high oleic sunflower oil (HOSF) and 1,3-diaminopropane prepared according to the method of Example 1.
Figure 7B:
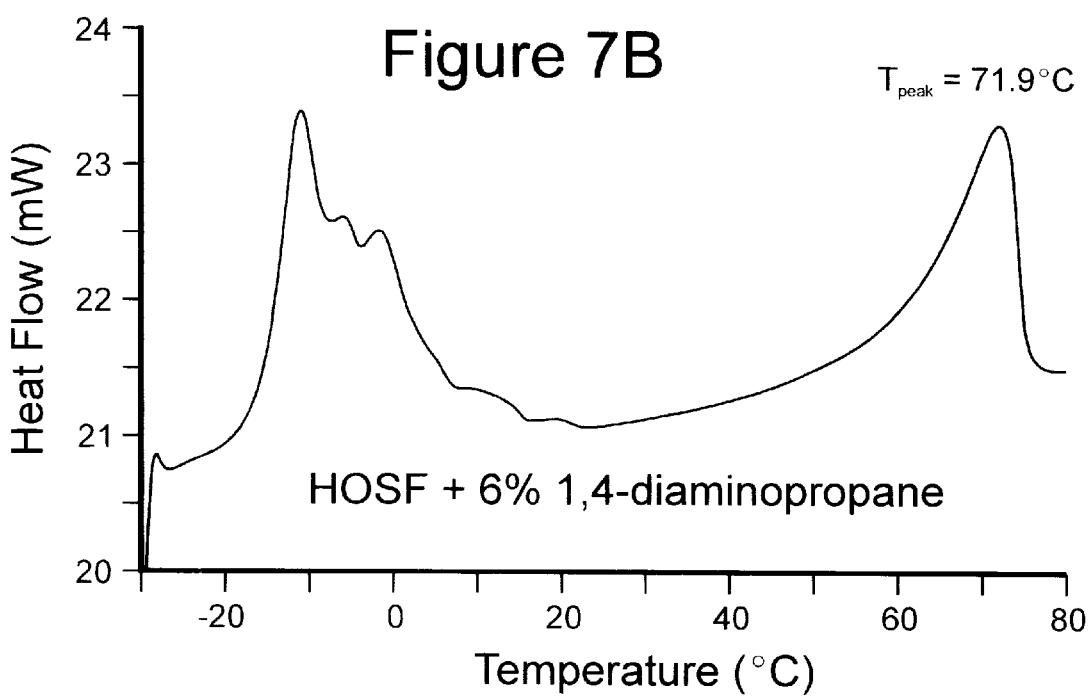

The peak melting point ($T_m$) of each treated sample was then determined by differential scanning calorimetry (DSC). The DSC analyses were performed with a Seiko Calorimeter Instrument, Model Perkin-Elmer DSC-7. The DSC protocol was as follows: (1) heated from 25° C. to an upper temperature limit (generally 80° C. or 120° C.) at rate of 10° C./min; (2) held for 5.0 minutes at the upper temperature limit; (3) cooled from the upper temperature limit to –30° C. at about 5° C./min; (4) held for 5.0 minutes at –30° C.; and (5) heated from –30° C. to the upper temperature limit at about 10° C./min. DSC thermograms were generated from the heat flow (mW) versus temperature (°C.); peak melting points for each sample was determined from the associated thermogram. FIG. 7 provides the representative thermograms obtained for lipid-polyamine structural matrixes of this invention. For each sample, the total percentage liquid present in the product mixture containing the lipid-polyamine structural matrix was determined at both 25° C. and 40° C. For comparison, the peak melting point of the high oleic sunflower oil (sample C1) alone (i.e., no added polyamine) was determined. The results of Samples 1–7 and control C1 are summarized in Table 1.

TABLE 1

| | | | Peak Melting | Total % liquid @ | |
|---|---|---|---|---|---|
| Sample | Polyamine | Fat | Point (° C.) | 25° C. | 40° C. |
| C1 | none | HOSF | — | 100.0 | 100.0 |
| 1 | AEAE | HOSF | 56.7 | 77.4 | 80.4 |
| 2 | APPD | HOSF | 59.0 | 66.1 | 69.6 |
| 3 | DAP | HOSF | 71.8 | 60.1 | 61.2 |
| 4 | DAB | HOSF | 88.8 | 68.4 | 69.8 |
| 5 | SMD | HOSF | 79.8 | 65.9 | 66.9 |
| 6 | SM | HOSF | 71.4 | 85.0 | 86.2 |
| 7 | BAPPDA | HOSF | 26.8 | 83.0 | 90.8 |

These results demonstrated the ability to form a lipid-polyamine mixture or complex that can exist in solid or semi-solid form at a higher temperature than the untreated lipid alone. The results also show that the inventive effects were not limited to the use of any particular polyamine. The results also demonstrated that a relatively wide range of melting point temperatures could be obtained among the produced solid (or semi-solid) fats by varying the polyamine treating agent employed for a given fatty oil.

Additionally, based on the DSC thermograms, the lipid-polyamine mixtures obtained by the process tended to have rounded curves encompassing several or more temperature values at the melt endotherm peak region instead of sharp spikes or peaks at a specific given temperature value. A single peak or highest melt temperature ($T_m$) value was readily indentifiable for the samples representing the invention. These observations indicated that a crystal lattice per se may not be present in the lipid-polyamine mixture and product obtained by the process. Rather, the thermograms of the samples representing the invention are consistent with the melt profile of a composite or semi-crystalline type of material.

EXAMPLE 2

Several different fatty oils having different degrees of unsaturation were investigated using 2-aminoethylamino) ethanol (AEAE). The fatty oils included high oleic sunflower oil (HOSF; the same as used in Example 1) soy bean oil (SBO), and fish oil (FO). The fish oil contained long chain polyunsaturated fatty acids including eicosapentaenoic acids (EPA) and decosahexaenoic acids (DHA). The SBO was obtained from Cargil Inc. (Minneapolis, Minn.); and the FO was obtained from Omega Protein Corp. (Hammond, La.).

Each oil was mixed with about 6 percent 2-(2-aminoethylamino) ethanol. The same experimental procedure was used as that described for Example 1. Peak melting points and the total liquid content percentage at two temperatures for these lipid-polyamine products were measured and the results are summarized in Table 2. The melting points of the untreated oils (samples C2, C2, and C4) were also determined.

TABLE 2

| | | | Peak Melting | Total % liquid @ | |
|---|---|---|---|---|---|
| Sample | Fat | Polyamine | Point (° C.) | 25° C. | 40° C. |
| 8 | HOSF | AEAE | 56.7 | 77.4 | 80.4 |
| C2 | HOSF | none | <25 | 100 | 100 |
| 9 | SBO | AEAE | 44.5 | 39.9 | 44.4 |
| C3 | SBO | none | <25 | 100 | 100 |
| 10 | FO | AEAE | 47.8 | 75.3 | 84.5 |
| C4 | FO | none | <25 | 100 | 100 |

The results from this example clearly demonstrated the ability to form a lipid-polyamine structural matrix having an increased melting point as compared to the lipid by itself was not limited to any particular fatty oil ingredient.

The results of Examples 1 and 2 also show that it is feasible to structurally assemble different polyamines with different liquids oil according to the invention to produce solid fats with melting points and solid fat contents that can be suited and customized to specific performance needs in mind.

EXAMPLE 3

Additional experimental studies were performed to investigate the thermo-reversibility of several representative lipid-polyamine composite matrix products prepared according to the invention. Separate fresh portions of each of Samples 1–7 (Example 1) was analyzed with DSC for thermo reversible behavior. Samples were loaded into DSC pans and heated up at a rate of about 10° C./minute until completely melted. This temperature was recorded for each sample. The heated samples were then rapidly cooled (i.e., to about −30° C. at about by 5° C./minute) to solidify the molten sample. The onset of solidification of the oil during supercooling was recorded as the peak of the melt endothermic peak region of the thermogram generated by the DSC analysis. The results are summarized in Table 3.

TABLE 3

| Sample | Polyamine | Fat | Peak Melting Point (° C.) | Onset of Solidification (° C.) |
|---|---|---|---|---|
| 1 | AEAE | HOSF | 21.2 | 36.9 |
| 2 | APPD | HOSF | 35.5 | 39.7 |
| 3 | DAP | HOSF | 56.2 | 62.9 |
| 4 | DAB | HOSF | 77.9 | 82.0 |
| 5 | SMD | HOSF | 65.8 | 68.8 |
| 6 | SM | HOSF | 47.9 | 53.0 |
| 7 | BAPPDA | HOSF | −10.0 | 0.0 |

These results demonstrate the thermo-reversibility of the lipid-polyamine composite matrix products of the invention. This thermo-reversible character of the inventive lipid-polyamine structural matrices makes them suitable for a wide range of applications in which conventional solid fats have been used, where the physical state of the lipid-polyamine mixture can be easily controlled and selected.

EXAMPLE 4

Samples 1–7 from Example 1 were also examined under polarized light (i.e., light microscopy). As seen in the microphotographs of FIGS. 1–6, a multiplicity of distinct regions appear where light is reflected by solid inclusions and/or particles present in the sample. For comparison, individual samples of the high oleic sunflower oil and each polyamine used in Samples 1–7 were viewed separately by light microscopy. The individual components were transparent upon light microscopy examination with no particles or inclusions being observed. Samples 9 and 10 of Example 2 were also subjected to light microscopy; similar solid inclusions or particles (i.e., composite lipid-polyamine molecular structures) were observed.

Comparison Example 1

The procedure of Sample 1 was duplicated except that 6 percent of monohexylamine was used in place of a polyamine. The melting point of the resulting mixture of the monoamine and HOSF was not noticeably different than that of HOSF by itself, and observation of the mixture by light microscopy after 12 hours revealed no presence of light reflective particles or inclusions.

While the invention has been described in terms of preferred embodiments, those skilled in the art will recognize that the invention can be practiced with modification within the spirit and scope of the appended claims.

What is claimed is:

1. A process for hardening a lipid, comprising mixing the lipid with an effective amount of a polyamine to form a mixture and allowing the mixture to stand for a time sufficient to form a hardened lipid having a higher peak melting point than the lipid alone.

2. The process according to claim 1, wherein the lipid is an unsaturated lipid.

3. The process according to claim 2, wherein the polyamine is present in the mixture at a level of at least about 1 percent and wherein the mixture does not contain a solvent or dispersion medium.

4. The process according to claim 3, wherein the polyamine is present in the mixture at a level of about 3 to about 10 percent.

5. The process according to claim 2, wherein the polyamine and lipid are mixed at a temperature between about 0 and about 100° C.

6. The process according to claim 5, wherein the polyamine and lipid are mixed at a temperature between about 10 and about 40° C.

7. The process according to claim 6, wherein the polyamine and lipid are mixed at a temperature between about 20 and about 30° C.

8. The process according to claim 2, wherein the mixture stands for at least about 10 hours after mixing.

9. The process according to claim 2, wherein the polyamine is an aliphatic polyamine.

10. The process according to claim 2, wherein the polyamine is represented by the formula:

$$NH_2-((CH_2)_p-(NH)_q-(CH_2)_r-(NH)_s-(CH_2)_t)_u-A$$

wherein u is an integer of 1 to 5; p, r and t independently are integers of 0 to 8, with the proviso that at least one of p, r, and t is greater than or equal to 2; wherein q and s independently are 0 or 1; and wherein A is an amino group, a hydroxyl group, or a fluoro group, with the proviso that, when A is hydroxyl or fluoro, at least one of q and s is 1.

11. The process according to claim 2, wherein the polyamine is selected from the group consisting of alkylene polyamines, imino polyalkylamines, and diimino polyalkylamines.

12. The process according to claim 11, wherein the polyamine is selected from the group consisting of alkylene diamines, alkylene triamines, alkylene tetraamines, alkylene pentamines, alkylene hexamines, and iminobis alkylamines.

13. The process according to claim 2, wherein the polyamine is putrescine, spermidine, spermine, or mixtures thereof.

14. The process according to claim 2, wherein the lipid is selected from the group consisting of unsaturated monoglycerides, unsaturated diglycerides, unsaturated triglycerides, unsaturated fatty acids, unsaturated fatty alcohols, unsaturated phosphatides, unsaturated sterols, unsaturated fat-soluble vitamins, unsaturated terpenes, and mixtures thereof.

15. The process according to claim 2, wherein the lipid is an unsaturated triglyceride.

16. The process according to claim 15, wherein the lipid is an oil selected from the group consisting of high oleic sunflower oil, sunflower oil, rapeseed oil, soybean oil, peanut oil, canola oil, cottonseed oil, coconut oil, palm oil, palm kernel oil, corn oil, flax seed oil, olive oil, safflower oil, lard oil, castor oil, fish oil, milk fat, beef tallow oil, and mixtures thereof.

17. A process for hardening an unsaturated triglyceride lipid, comprising the steps of:

(a) mixing an unsaturated triglyceride with an effective amount of an aliphatic polyamine to form a mixture, wherein said polyamine is added in an amount of at least about 1 percent based on total weight of said mixture;

(b) permitting the mixture to stand at a temperature of between about 0 and about 100° C. until the mixture acquires a higher peak melting point than the unsaturated triglyceride alone.

18. The process according to claim 17, where the mixture stands at the temperature for at least about 10 hours.

19. The process according to claim 17, wherein the polyamine is represented by the formula:

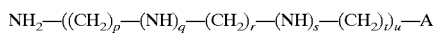

wherein u is an integer of 1 to 5; p, r and t independently are integers of 0 to 8, with the proviso that at least one of p, r, and t is greater than or equal to 2; wherein q and s independently are 0 or 1; and wherein A is an amino group, a hydroxyl group, or a fluoro group, with the proviso that, when A is hydroxyl or fluoro, at least one of q and s is 1; and wherein the unsaturated triglyceride is an oil selected from the group consisting of high oleic sunflower oil, sunflower oil, rapeseed oil, soybean oil, peanut oil, canola oil, cottonseed oil, coconut oil, palm oil, palm kernel oil, corn oil, flax seed oil, olive oil, safflower oil, lard oil, castor oil, fish oil, milk fat, beef tallow oil, and mixtures thereof.

20. A structured lipid system comprising a combination of an unsaturated lipid and an effective amount of a polyamine in which molecules of the polyamine and unsaturated lipid are arranged as a composite structural matrix, wherein the combination has a higher peak melting point than the unsaturated lipids alone.

21. The structured lipid system according to claim 20, wherein effective amount of the polyamine is at least about 1 percent.

22. The structured lipid system according to claim 20, wherein effective amount of the polyamine is at least about 1 percent.

23. The structured lipid system according to claim 22, wherein effective amount of the polyamine is about 1 to about 30 percent.

24. The structured lipid system according to claim 20, wherein the unsaturated lipid is an unsaturated triglyceride and the polyamine is an aliphatic polyamine.

25. The structured lipid system according to claim 23, wherein the unsaturated lipid is an unsaturated triglyceride and the polyamine is an aliphatic polyamine.

26. The structured lipid system according to claim 24, wherein the polyamine is represented by the formula:

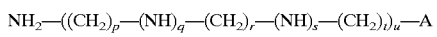

wherein u is an integer of 1 to 5; p, r and t independently are integers of 0 to 8, with the proviso that at least one of p, r, and t is greater than or equal to 2; wherein q and s independently are 0 or 1; and wherein A is an amino group, a hydroxyl group, or a fluoro group, with the proviso that, when A is hydroxyl or fluoro, at least one of q and s is 1; and wherein the unsaturated lipid is selected from the group consisting of high oleic sunflower oil, sunflower oil, rapeseed oil, soybean oil, peanut oil, canola oil, cottonseed oil, coconut oil, palm oil, palm kernel oil, corn oil, flax seed oil, olive oil, safflower oil, lard oil, castor oil, fish oil, milk fat, beef tallow oil, and mixtures thereof.

27. The structured lipid system according to claim 25, wherein the polyamine is represented by the formula:

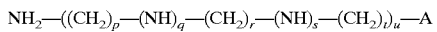

wherein u is an integer of 1 to 5; p, r and t independently are integers of 0 to 8, with the proviso that at least one of p, r, and t is greater than or equal to 2; wherein q and s independently are 0 or 1; and wherein A is an amino group, a hydroxyl group, or a fluoro group, with the proviso that, when A is hydroxyl or fluoro, at least one of q and s is 1; and wherein the unsaturated lipid is selected from the group consisting of high oleic sunflower oil, sunflower oil, rapeseed oil, soybean oil, peanut oil, canola oil, cottonseed oil, coconut oil, palm oil, palm kernel oil, corn oil, flax seed oil, olive oil, safflower oil, lard oil, castor oil, fish oil, milk fat, beef tallow oil, and mixtures thereof.

* * * * *

UNITED STATES PATENT AND TRADEMARK OFFICE
CERTIFICATE OF CORRECTION

PATENT NO.    : 6,479,684 B1
DATED         : November 12, 2002
INVENTOR(S)   : Akashe et al.

It is certified that error appears in the above-identified patent and that said Letters Patent is hereby corrected as shown below:

Column 14,
Lines 39-40, change "pol-yarnine" to -- polyamine --.

Signed and Sealed this

Eleventh Day of March, 2003

JAMES E. ROGAN
*Director of the United States Patent and Trademark Office*